United States Patent
Banerjee et al.

(10) Patent No.: US 6,589,780 B2
(45) Date of Patent: Jul. 8, 2003

(54) BIO-REACTOR FOR ENHANCING THE BIOMASS YIELD OF PLANT ORGANS

(75) Inventors: Suchitra Banerjee, Lucknow (IN); Arun Kumar Kukreja, Lucknow (IN); Praveen Chandra Verma, Lucknow (IN); Atul Prakash Kahol, Lucknow (IN); Sushil Kumar, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/736,434

(22) Filed: Dec. 15, 2000

(65) Prior Publication Data

US 2002/0076815 A1 Jun. 20, 2002

(51) Int. Cl.$^7$ ................................................ C12N 5/00
(52) U.S. Cl. .............................. 435/289.1; 435/293.2; 435/410; 47/58.1
(58) Field of Search ......................... 435/289.1, 293.2, 435/410; 42/58.1

(56) References Cited

U.S. PATENT DOCUMENTS

| | | | |
|---|---|---|---|
| 4,760,028 A | | 7/1988 | Debruyne et al. |
| 4,840,905 A | | 6/1989 | Kearns et al. |
| 5,030,573 A | | 7/1991 | Petiard et al. |
| 5,075,234 A | | 12/1991 | Tunac |
| 5,403,742 A | | 4/1995 | Freeman |
| 5,846,829 A | | 12/1998 | Worden et al. |
| 5,885,826 A | | 3/1999 | Worden et al. |
| 5,939,313 A | * | 8/1999 | Chen |
| 6,001,642 A | | 12/1999 | Tsao |
| 6,008,010 A | | 12/1999 | Greenberger et al. |
| 2002/0033543 A1 | * | 3/2002 | Batterham et al. |

OTHER PUBLICATIONS

Dilorio et al., Growth of transformed roots in a nutrient mist bioreactor. Reactor performance and evaluation. Appl. Micobiol. Biotechnol. 37: 457–462 (1992).

Muranaka T., Ohkawa H., Yamada Y., Continuous production of scopolamine by a culture of Duboisia leichharditii hairy root clone in a bioreactor system. Appl. Microbiol. Biotechnol. 40: 219–223 (1993).

Rodriguez–Mendiola M.A., Stafford, A., Cresswell, R., & Arias–Castro, C., Bio–reactors for growth of plant roots. Enzyme Microb. Technol. 13: 697–702. (1991).

Mckelvey, S.A., Gehrig, J.A., Hollar, K.A., and Curtis, W.R., Growth of Plant roots cultures in liquid and gas – dispersed reactor environment, Biotechnol. Prog. 9,317, 1993.

Hilton, M.C. and Rhodes M.J.C., Growth and hyoscyamine production of hairy root cultures of *Datura stramonium* in modified stirred tank reactor. Appl. Microbiol. Biotechnol. 33: 132–138 (1990).

Wayne R. Curtis, Cultivation of roots in bioreactors, Curr: Opinion in Biotechnol., vol. 4, pp. 205–210 (1993).

Leena Toivonen, Utilization of hairy root cultures for production of secondary metabolites, Biotechnol. Progr. 1993, 9, 12–20.

Jung, G. and Tepfer D., Use of genetic transformations by the RiT–DNA of *Agrobacterium rhizogenes* to stimulate biomass and tropane alkaloid production in *Atropa belladonna* and *Calystegia sepium* roots grown in vitro. Pl. Sci., 50: 145–151 (1987).

Singh, G. and Curtis, W.R. Reactor design for plant root cultures. In: Ngo that T. and Sbargool Peter D. (eds) Biotechnological application of plant cell cultures 1994, pp. 185–206. CRC Press. Inc.

* cited by examiner

Primary Examiner—Leon B. Lankford, Jr.
(74) Attorney, Agent, or Firm—Greenblum & Bernstein, P.L.C.

(57) ABSTRACT

A bio-reactor for enhancing the biomass yield using a closed sterile vessel having a medium, said reactor comprising a central shaft, a support matrix oriented horizontally and dividing the vessel into an upper and a lower chamber, a means for stirring selected from turbine-2,4,6-impeller; marine blade impeller; helical blade impeller; mounted onto the central shaft and located at a predetermined distance from the support matrix so as to generate both radially and axially directed volumetric flow of the media; and at least two semi-circular spargers located both in the upper and lower compartments of the vessel at a predetermined distance from the support matrix.

12 Claims, 9 Drawing Sheets

BAFFLE ASSEMBLY

CONVENTIONALLY USED TURBINE
IMPELLER WITH FOUR BLADES

CONVENTIONALLY USED TURBINE
IMPELLER WITH FOUR BLADES

RADIAL FLOW GENERATED BY TURBINE IMPELLER

RING SPARGER

CROSS-SECTION VIEW
MARINE IMPELLER

TOP VIEW
MARINE IMPELLER

AXIAL FLOW AND RADIAL FLOW GENERATED BY
MARINE IMPELLER

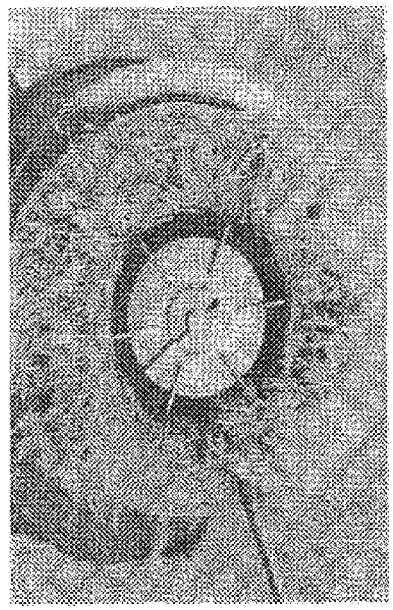

UP-SCALING OF H. muticus HAIRY ROOT LINE M-7 IN THE MODIFIED MECHANICALLY AGITATED (TURBINE IMPELLER), AIR-SPARGED BIOREACTOR WITH INCLUSION OF A CENTRAL SUPPORT MATRIX SHOWING ROOT GROWTH RETARDATION IN THE AREA BETWEEN TURBINE IMPELLER & NYLON MESH (FOUR WEEKS AFTER CULTIVATION).

FIG 8(A)

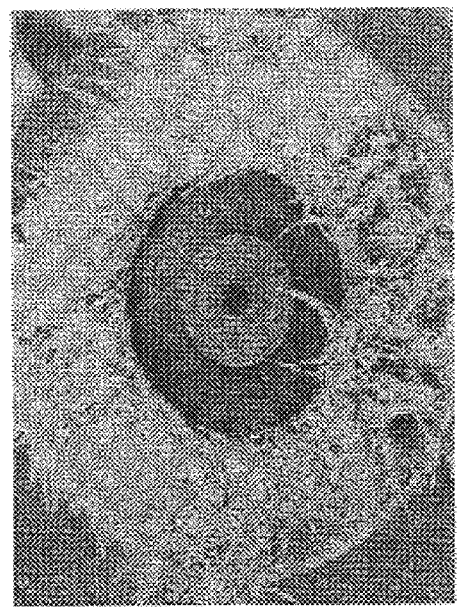

UP-SCALING OF H. muticus HAIRY ROOT LINE M-7 IN THE MODIFIED MECHANICALLY AGITATED (TURBINE IMPELLER), AIR-SPARGED BIOREACTOR WITH INCLUSION OF A CENTRAL SUPPORT MATRIX SHOWING ROOT GROWTH RETARDATION IN THE AREA BETWEEN TURBINE IMPELLER & NYLON MESH (FOUR WEEKS AFTER CULTIVATION).

FIG 8(B)

SUCCESSFUL UP-SCALING OF H. muticus HAIRY ROOT LINE M-7 THROUGH INSTALLATION OF A MARINE IMPELLER IN THE CENTRAL SHAFT OF THE UPPER COMPARTMENT (FOUR WEEKS AFTER CULTIVATION).

SUCCESSFUL UP-SCALING OF H. muticus HAIRY ROOT LINE M-7 THROUGH INSTALLATION OF A MARINE IMPELLER IN THE CENTRAL SHAFT OF THE UPPER COMPARTMENT (FOUR WEEKS AFTER CULTIVATION).

UP-SCALING OF *Valerinana wallichii* HAIRY ROOT LINE V-4G IN THE MODIFIED AIR SPARGED, PARTIALLY AGITATED (MARINE IMPELLERS BOTH IN UPPER AND LOWER COMPARTMENTS) BIOREACTOR WITH CENTRAL SUPPORT MATRIX (FOUR WEEKS CULTIVATION).

FIG 10(A)

UP-SCALING OF *Valerinana wallichii* HAIRY ROOT LINE V-4G IN THE MODIFIED AIR SPARGED, PARTIALLY AGITATED (MARINE IMPELLERS BOTH IN UPPER AND LOWER COMPARTMENTS) BIOREACTOR WITH CENTRAL SUPPORT MATRIX (FOUR WEEKS CULTIVATION).

FIG 10(B)

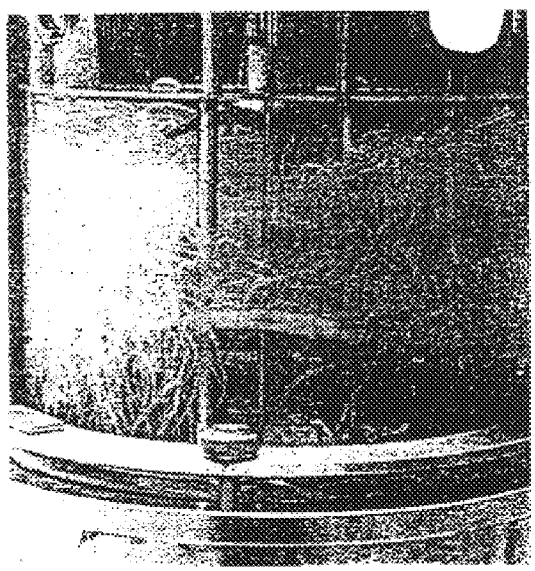

UP-SCALING OF *Rouvolfia serpentina* HAIRY ROOT LINE Sn-3 AT pH 5.86 IN A MODIFIED AIR SPARGED MECHANICALLY AGITATED (MARINE IMPELLER BOTH IN THE UPPER AND LOWER COMPARTMENTS) BIOREACTOR WITH CENTRAL SUPPORT MATRIX
(FOUR WEEKS AFTER CULTIVATION).

FIG 11(A)

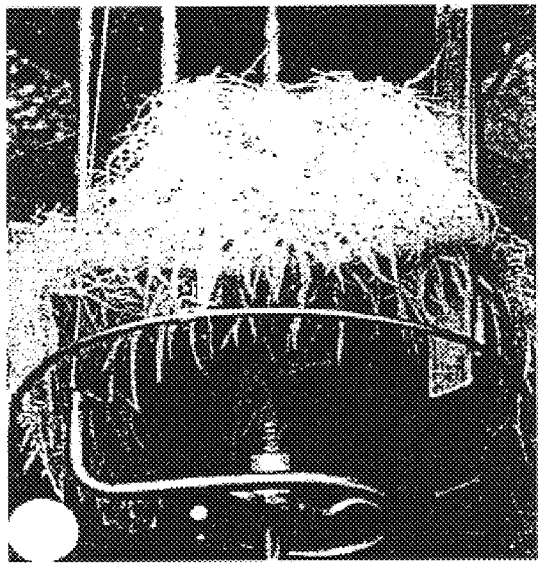

UP-SCALING OF *Rouvolfia serpentina* HAIRY ROOT LINE Sn-3 AT pH 5.86 IN A MODIFIED AIR SPARGED MECHANICALLY AGITATED (MARINE IMPELLER BOTH IN THE UPPER AND LOWER COMPARTMENTS) BIOREACTOR WITH CENTRAL SUPPORT MATRIX
(FOUR WEEKS AFTER CULTIVATION).

FIG 11(B)

BIO-REACTOR FOR ENHANCING THE BIOMASS YIELD OF PLANT ORGANS

BACKGROUND

1. Field of the Invention

The present invention relates a novel bio-reactor and more particularly to an apparatus or system for cultivation and up-scaling of genetically transformed plant organ (root) or parts in a sterile artificial environment, e.g. aqueous growth medium and to novel methods of employing the apparatus. The apparatus or vessel of the invention affords high aeration capacity through novel air dispersing and sparging systems. The high dispersion of air in the liquid medium is attainable at low agitation speed with the advantage of creating low shear thereby being favorable for the growth of highly entangled hairy root cultures.

2. Prior Art of the Invention

Considerable efforts are now being paid towards up-scaling of transgenic hairy root cultures of diverse plant species. Several publications are now available describing the use of different kinds of bio-reactors with or without design modification such as Singh, G. and Curtis, W. R. Reactor design for plant root cultures In: Ngo that T. and Sbargool Peter D. (eds.) Biotechnological application of plant cell cultures 1994 pp.-185–206. CRC Press, Inc.; Toivonen L., Utilization of hairy root cultures for production of secondary metabolites. Biotechnol. Prog. 9: 12–20 (1993), and Curtis, W. R., Cultivation of roots in bio-reactors. Curr. Opinion in Biotechnol. 4; 205–210 (1993).

The number of reports of hairy root culture in bio-reactors has increased significantly within the last few years. From a detailed literature survey it has been found that hairy roots have been cultivated in a wide range of reactor configurations varying from novel construction to simple modifications of the existing ones. Mainly two types of reactors have been used for hairy root up-scaling, i.e. bubble column reactors have been successfully used to culture hairy roots of *Tagetes patula, H. mulicus* and *Lithospermum erythrorhizon* (Buitelaar et al;1991, Mckelvey et al;1993;1992, Shimomura et al; 1991). However, when compared with other types of reactors, the performance of the bubble column reactors was rather poor (Taya et al; 1989, Weathers et al; 1989). The poor performance may be due to low oxygen supply because of channeling or tissue damage caused by sparging.

Although the other type of reactor, i.e. mechanically agitated one performed well in case of *Tagetes patula* (Buitelaar et al; 1991) the final tissue densities were limited in these systems due to mechanical damage of tissue caused mostly by the use of turbine impeller (Taya et al; 1989 and Wilson et al;1990).

Isolated impeller reactors in which the impeller is prevented from coming in contact with the root mass by using stainless steel mesh, polyurethane foam, etc., performed quite well in a number of cases (Muranaka et al; 1993, Inomata et al; 1993, Taya et al; 1989, Jung et al; 1987 & Hilton et al; 1990).

However, as with other reactor constructions, it can be anticipated that there will be numerous problems associated with high-density culture with regard to providing sufficient mixing in such systems (Singh & Curtis, 1994).

There are certain other reactor configurations which substantially differ from the conventional sparged or mechanically agitated type. Such reactors are mainly of two types- tickle bed and ebb- and -flow type, both of which are tried to provide both wetting and gas-contacting steps (Flores et al, 1992, Wilson et al; 1987, Taya et al; 1989, Cuello et al 1991, Dilorio et al; 1992a,b). Similar problems of gas we well as liquid phase channeling, as normally been encountered in case of the bubble column and stirred tank reactors, interfere with the final biomass yield. On the basis of the overall analysis, it becomes clear that the performance of all these reactors will be dependent on the ability to provide sufficient wetting of the densely packed, interconnected hairy root matrix for both nutrients as well as oxygen availability.

On the background of this information, it was felt essential to invent some modifications which would enable us to overcome the shortcomings keeping the other advantages of isolated impeller reactors constant.

OBJECTS OF THE INVENTION

The main object of this invention is to provide a novel bio-reactor to maximize genetically transformed "hairy root" biomass yield through up-scaling.

Another object of the present invention is to provide novel and improved systems/apparatus for the growth and cultivation of "hairy root" cultures affording efficient oxygen and nutrient distribution capacity throughout the reactor vessel, superior to conventional fermentors or bio-reactors.

Yet another object of the present invention is to provide improved oxygen and nutrient supply at low shear to prevent damage of shear-sensitive tissues of "hairy root" cultures.

Still another object of the present invention is to provide means for suppression of air-pocket formation so as to avoid the problem of gas channeling.

One more object of the present invention is to facilitate the supply of both oxygen and nutrients to the regions of highest tissue density so as to avoid starvation and death of "hairy root" tissues leading to poor productivity.

These and other objects, features and advantages of the invention will be seen from the following description and accompanying figures.

SUMMARY OF THE INVENTION

To meet the above objects, the present invention provides a novel bio-reactor comprising special type of impellers and sparges located at particular locations and an uniform support matrix present in the bio-reactor.

DETAILED DESCRIPTION OF THE INVENTION

Considerable interest is now being shown in *Agrabacterium rhizogenes* induced hairy root cultures for the production of high value plant secondary products. These cultures show a high degree of genetic stability, grow rapidly in hormone free culture medium with profusion of lateral branching and most importantly produce the same spectrum of secondary metabolites in quantities equivalent to or even in higher amounts than that of the parent plant (Hamill et al., 1986). So far several attempts have been reported for up-scaling of hairy roots in fermentors (Singh and Curtis 1994; Banerjee et al., 1995). Almost all such studies demonstrated the ability to grow hairy root cultures in bio-reactors and at the same time, discussed briefly the problems encountered which comprehensively indicate the scope for further improvement. In order to meet this need, the present invention is a process for up-scaling of hairy roots in a modified bio-reactor in order to take care of the earlier encountered problems.

In addition to the tissue culture multiplication steps and growth media constituents which are known in the art, an essential step of the preferred embodiment of the invention includes selection of a special type of impeller from the group consisting of turbine or rouston blade-2, 4, 6; marine blade, helical blade and pitched blade turbine impeller. In all embodiments of the invention, however, it is believed that the effectiveness of the present invention is attributable, at least in part, to the position and number of the special type of impeller as well as that of the spargers. The invention also describes a bio-reactor using low cost, autoclavable support matrix in order to isolate the impeller from growing roots as well as for uniform distribution and growth of the hairy root. The hairy roots preferably be obtained from *Hyoscyamus muticus, H. albus, R. seripentina* and *V. wallichii, Atropa belladonna* and *A. accuminata*.

*Agrobactrium rhizogenes* induced hairy root cultures of a wide variety of plant systems have already proved to be an excellent alternative production system for plant-derived chemical. However both advantages and disadvantages have been found to be associated with their higher level of culture differentiation. The primary advantage of hairy root cultures is that they display the tremendous biosynthetic capacity of normal roots with stable-long-term product profile, which is attributed to their higher level of cellular differentiation as compared to plant cell/suspension culture. These characteristics along with their faster growth rate signify their economic advantages over that of normal plant cultivation, especially for the endangered plant species.

Although the cellular differentiation provides the hairy roots, the advantages of metabolic and physical stability, it also imparts several disadvantages of which creation of physical barrier to transport properties due to formation of net like root matrix which captures and coalesces the bubbles to form air pockets throughout the reactor vessel, is the primary one. Since scale-up of such highly entangled hairy root cultures depend upon the ability to achieve even nutrient distribution to roots over very large dimensions, refinement in the media and gas flow patterns within the reactor vessel needs special attention which has been taken care of in course of the present invention.

In order to avoid clumping of hairy roots at certain regions and to ensure even distribution of roots within the reactor vessel, a support matrix has been incorporated. The support matrix can be chosen from autoclavable nylon mesh, stainless steel mesh, polyurethane foam etc. Besides anchorage and even distribution of the roots, such support matrix also offers other advantages amongst which isolation of the impeller thereby preventing shear damage to the root tissue needs special mention. Use of such support matrix has got commercial viability since it can be continuously used for several experiments and also can be renewed with minimum cost.

The method of this invention for enhancing the hairy roots biomass yield involves the use of a specific impeller at specific site so as to nullify or reduce the barrier to transport properties within the reactor vessel. The flow pattern generated by such specific impeller being both axial and radial, the flow of the media can more forcefully be directed through the regions of higher tissue densities due to its powerful volumetric flow. The typical impeller may be chosen from the marine or pitched-blade turbine one and its position may be within the vessel or away from the same. Position of the impeller and the flow pattern generated by the same decides the effectiveness of its use over the others in terms of even distribution of nutrient and oxygen over larger dimensions.

The present invention enables the medium in the vessel to be mixed and aerated effectively with substantially being more efficiently distributed through out the reactor vessel as well as though the densely packed hairy root tissues than heretofore possible by conventional means.

This invention relates to a method for enhancing the transgenic hairy root biomass yield without the use of growth regulators but through use of a specific type of impeller [not earlier been used for hairy root culture] at specific position, thus limiting the shearing effect along with variable number of sparger and specially support matrix which allowed uniform distribution of hairy roots within the reactor and helped to overcome the problem of formation of air pockets and channelisation of the oxygenated media.

The process according to this invention is capable of providing a plurality of enhancing the biomass yield of the hairy roots of several medicinal plants, which include *Hyoscyamus muticus, H. albus, Valeriana wallichii, Rauwolfia serpentina, Atropa belladonna, A. acuminata* etc. The present invention provides rapid, reliable, commercially viable technique which, for whatever reason, could not be achieved according to the methods of the prior art.

Accordingly, the present invention provide a bio-reactor for enhancing the biomass yield using a closed sterile vessel having a medium, said reactor comprising a central shaft, a support matrix oriented horizontally and dividing the vessel into an upper and a lower chambers, a means for stirring selected from turbine-2, 4, 6 impeller; marine blade impeller or helical blade impeller mounted onto the central shaft and located at a predetermined distance from the support matrix so as to generate both radially and axially directed volumetric flow of the media, and at least two semi-circular spargers located both in the upper and lower compartments of the vessel at a predetermined distance from the support matrix.

Preferably, the invention relates to a bio-reactor for enhancing the growth of genetically transformed hairy root of plants in a culture medium without the use of growth regulators, which comprises a glass culture vessel for aqueous growth medium having a central shaft, and inner side wall which is radially symmetrical about a central vertical axis, at least one elongated baffle assembly fixed in an offset position on the vessel sides, so as to subdivide the inner side wall into equal parts and to cause rotary transport of the radially flowing aqueous medium contained in the vessel and to prevent vortex formation; the said culture vessel being divided into lower and upper compartment by fixing a support matrix on the baffle assembly to prevent damage, disformation, shearing and subsequent loss of productive capacity of hairy roots; two marine blade impellers being positioned on the central shaft one in the upper chamber within a pre-determined distance from a head plate and dipped in the medium, and other in the lower chamber at a pre-determined distance above the end of the central shaft to cause both axial and radial flow of aqueous medium contained in the vessel, and double elongated semi-circular spargers, one is located in the upper chamber and the other is located in the lower chamber of the vessel for the purpose of proper oxygenation of the culture medium.

In an embodiment of the present invention, the vessel of the bio-reactor is a conventional one, the dimensions of the vessel are applicable to our invention also. The bio-reactor is converted with a head plate.

In another embodiment of the present invention, the support matrix may be selected from stainless steel mesh, polyurethane foam or autoclavable nylon mesh.

In still another embodiment of the present invention, the baffle assembly has four vertical plates connected by one or more connecting means.

In yet another embodiment of the present invention, the stirrer blade may be selected from turbine (2,4,6) helical, marine or pitched turbine impeller.

In one more embodiment of the present invention, the first marine blade impeller is located on the central shaft within a distance ranging between 8–10 cm from the head plate.

In another embodiment of the present invention, the other marine blade impeller is located in the lower portion at about 4 cm above the end of the central shaft.

In yet another embodiment of the present invention, pair of semicircular spargers extend both in the upper and lower chambers, positioned at a certain distance from the central support matrix.

In still another embodiment of the present invention, the spargers may be equidistant from the central support matrix or may be at varied distances.

In still another embodiment of the present invention, the experimental hairy roots may be selected from either of the following plants; *Hyoscyamus muticus, H. albus, Valeriana wallichii, Rauwolfia serpentina, Atropa belladonna, A. accummata*.

The present bio-reactor is not a obvious modification. In fact, after much experimentation the inventors have arrived at the present invention. In deed, after much effort, the inventors are able to establish that use of a particular type of stirrer selected by the inventors and located at a specific position along with the use of a support matrix and multiple aeration ports are critical factors for maximum yield of hairy root biomass.

The invention is described in detail in the following description and example which are provided to illustrate the invention and therefore these should not be construed to limit the scope of the invention.

BRIEF DESCRIPTION OF THE DRAWINGS

FIGS. 8(a) and 8(b) show up-scaling of *H. muticus* hairy root.

FIGS. 10(a) and 10(b) show up-scaling of *Valeriana wallichii* hairy root in a conventional bio-reactor.

FIGS. 11(a) and 11(b) show successful up-scaling of *Rauwolfia serpentina* hairy root using the novel bio-reactor comprising a marine impeller.

DESCRIPTION OF THE PREFERRED EMBODIMENTS

Figure 1:
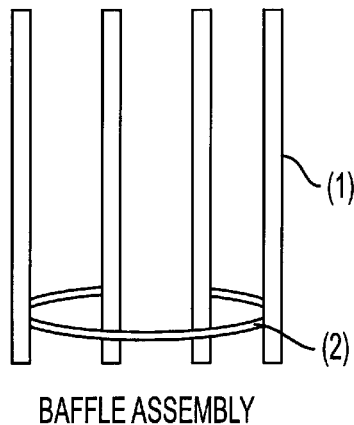
FIG. 1 shows a baffle assembly, which can be located inside the bio-reactor.
Figure 2A:
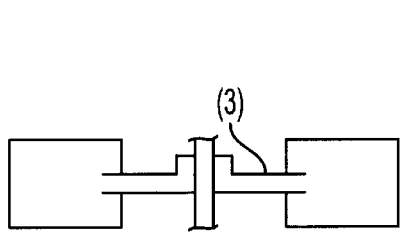
FIGS. 2(a) and 2(b) show conventional turbine impeller.
Figure 2B:
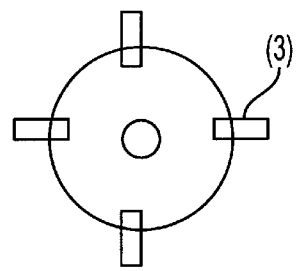
Figure 3:
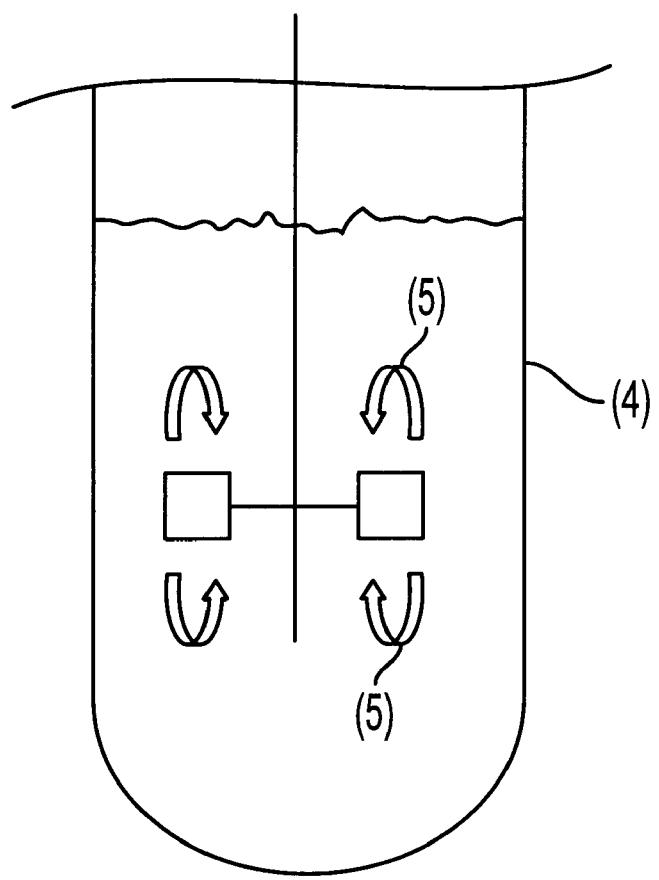
FIG. 3 shows radial flow generated by conventional turbine impeller.
Figure 4:
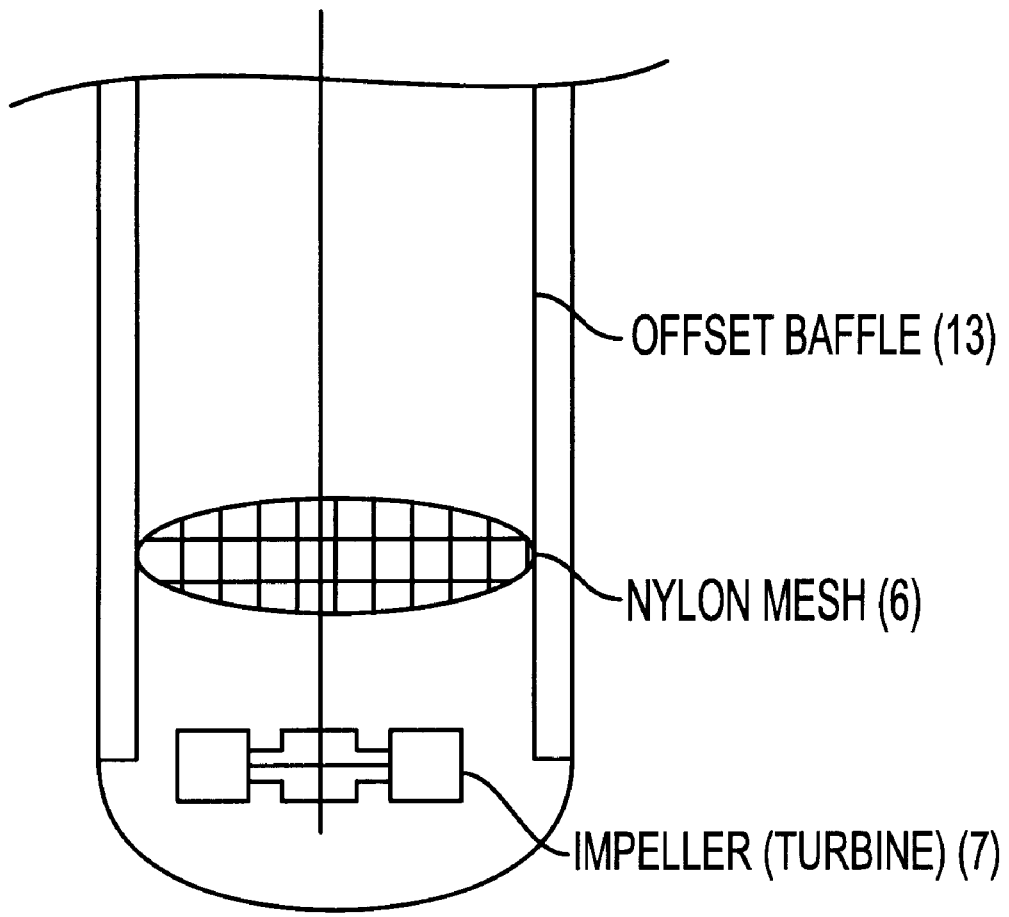
FIG. 4 shows the novel bio-reactor having the baffle assembly, nylon mesh and an impeller turbine.
Figure 5:
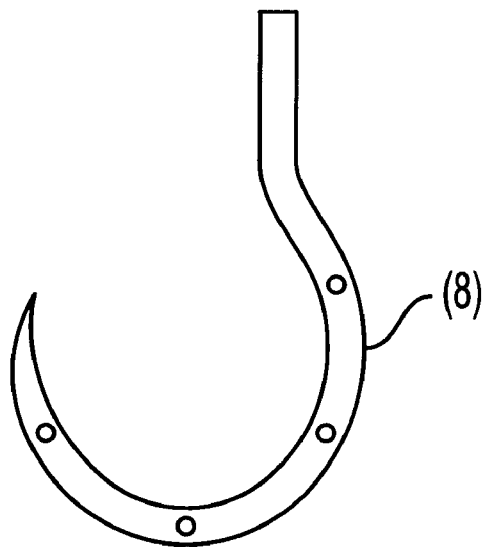
FIG. 5 shows a ring sparger.
Figure 6A:
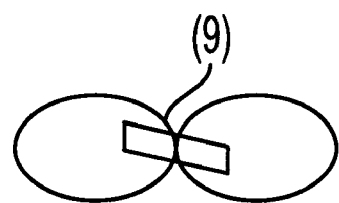
FIGS. 6(a) and 6(b) show marine impeller used in the present invention.
Figure 6B:
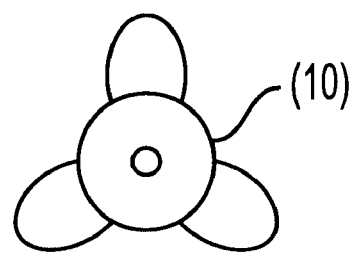
Figure 7:
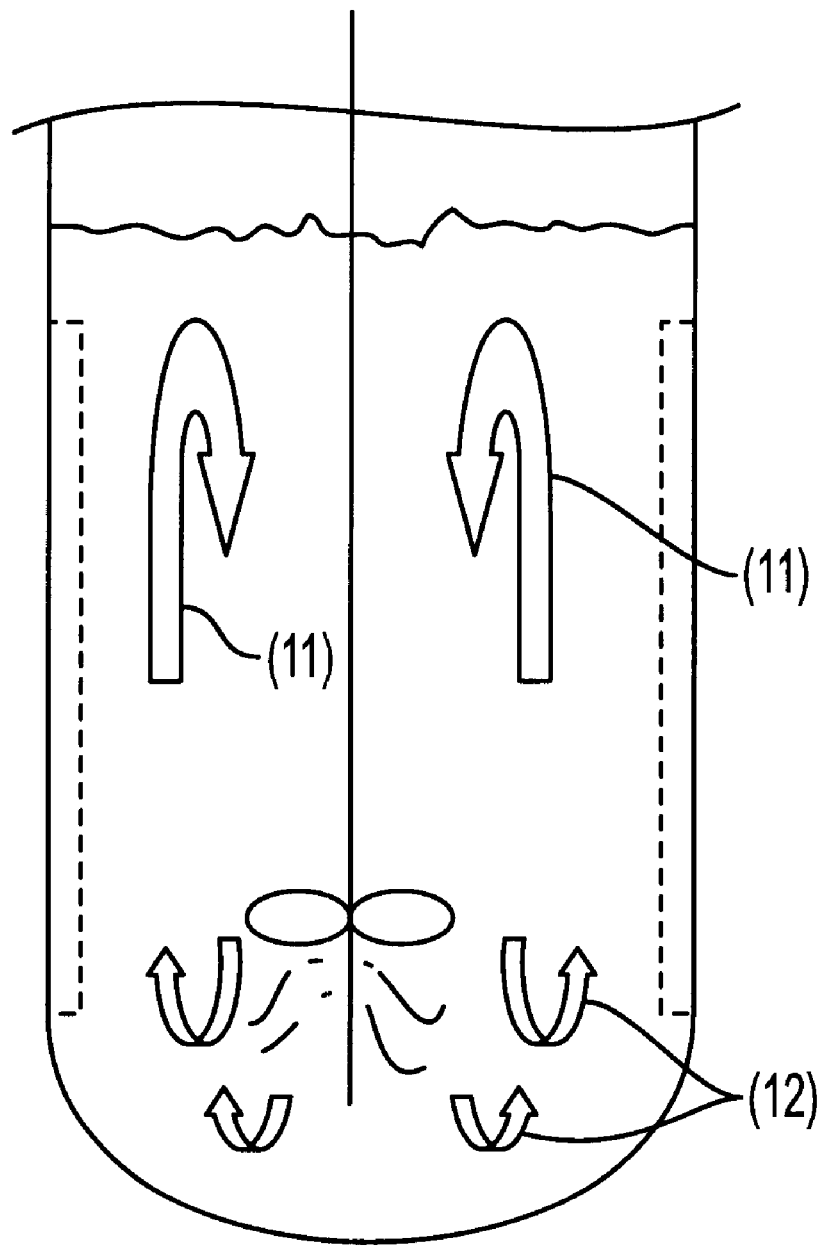
FIG. 7 shows the axial flow and radial flow generated by use of marine impeller in the bio-reactor.
Figure 9A:
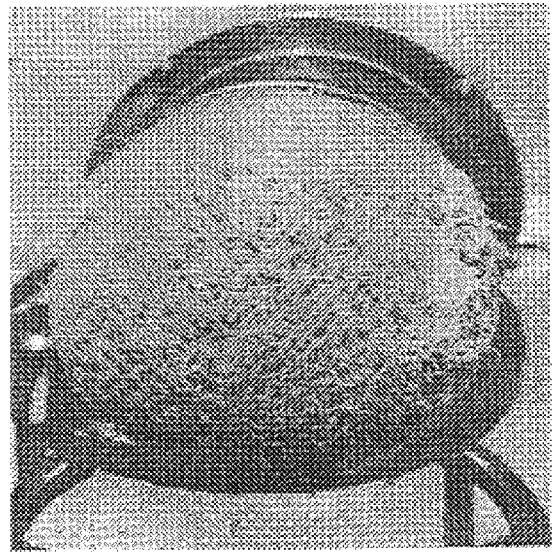
FIGS. 9(a) and 9(b) show successful up-scaling of *H. muticus* hairy root using the novel bio-reactor comprising a marine impeller.
Figure 9B:
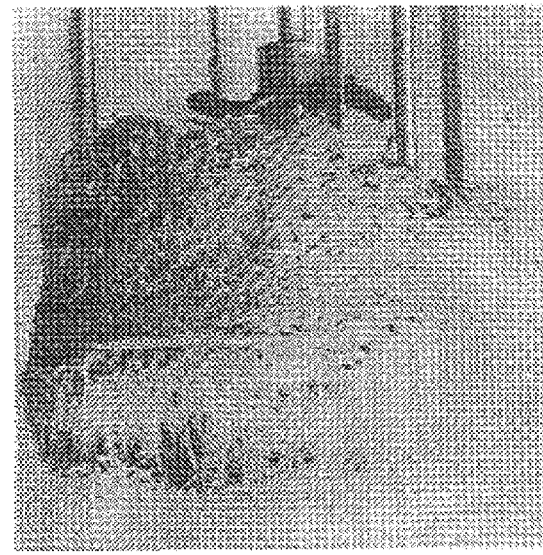

FIG. 1 shows a baffle assembly having vertical plates (1) preferably 4 in number, which are kept at equal distance. The vertical plates are linked to one another by horizontally placed rings (2). The baffle assembly is placed inside the bio-reactor, which provides radial flow of aqueous medium present in the vessel and at the same time, to prevent vortex formation. FIGS. 2(a) and 2(b) show the blade configuration (3) of conventionally used turbine impeller having four blades. FIG. 3 shows a conventional bio-reactor (4) having turbine impeller with four blades. When in operation, the rotation of the blades provide mere radial flow (5) of aqueous medium present in the tube. FIG. 4 shows a bio-reactor of the present invention. This figure clearly shows the location of the baffle assembly (13) in an offset position, a nylon mesh (6) and an impeller turbine (7). FIG. 5 shows a ring sparger (8) for supplying gas. FIGS. 6(a) and 6(b) show the cross-section (9) and top (10) views of three blade marine impeller used in the present invention. The operational details on the novel bio-reactor is clearly shown in FIG. 7. By viewing this figure, the axial flow (11) and radial flow (12) of the aqueous solution present in the vessel can be observed. FIGS. 8(a) and 8(b) show up-scaling of *H. muticus* hairy root line M-7 in a modified mechanically agitated (turbine impeller), air-sparged bio-reactor with inclusion of a central support matrix showing root growth retardation in the area between turbine impeller & nylon mesh (Four weeks after cultivation). FIGS. 9(a) and 9(b) show successful up-scaling of *H. muticus* hairy root line M-7 through installation of a marine impeller in the central shaft of the upper compartment (Four weeks after cultivation). FIGS. 10(a) and 10(b) show up-scaling of *Valariana wallichii* hair root line V-4G in the modified airsparged, partially agitated (marine impellers both in upper and lower compartments) bio-reactor with central support matrix (Four weeks after cultivation). FIGS. 11(a) and 11(b) show up-scaling of *Rauwolfia serpentina* hairy root line Sn-3 at pH 5.86 in a modified air sparged mechanically agitated (marine impeller both in the upper and lower compartments) bio-reactor with central support matrix (Four weeks after cultivation).

EXAMPLE

Hairy roots of *Hyoscyamus muticus*, initiated through genetic transformation by *Agrobacterium rhizogenes* strain A4, were cultured in liquid half strength Murashige and Skoog's (1962) medium without any hormone in gyratory shake flasks at 25±2° C. under dark condition. Two weeks old hairy root culture was aseptically inoculated in a 5 liter bioreactor, which was assembled and autoclaved earlier. The medium used in the reactor was same as in the shake flask. The configuration of the reactor was modified according to the following: An apparatus for enhancing the growth of genetically transformed hairy root in a culture medium of a medicinal plants without the use of growth regulators which comprises:

a) An open glass culture vessel for aqueous growth medium having top and bottom ends and inner side walls that is radially symmetrical about a central vertical axis.

b) At least one elongated baffle assembly to be (four baffles per vessel) fixed in an offset position on the vessel sides, so as subdivide the inner side wall into four equal quadrants.

c) The culture vessel divided in to lower and upper compartment by fixing a support matrix on the lower stainless steel semicircular baffle assembly to prevent damage, disformation, and shearing and subsequent loss of productive capacity of hairy roots.

d) Two marine blade impellers were positioned on the central shaft, one in the upper chamber, within a distance ranging between 8–10 cm from the head plate, dipped in the medium and other in the lower position, about 4 cm above the end of the central shaft, to cause both and axial radial flow of aqueous medium contained in the vessel.

e) Use of double elongated sparger instead of a single sparger; one in upper and other in lower chamber of the vessel for the purpose of oxygenation of the aqueous medium.

The airflow was maintained at 1.5 l/min and the agitator was kept constant at 50 rpm. After 28 days of culture the culture was harvested and the fresh weight and dry weight increase was calculated.

FIG. 8 uses turbine blade impeller.

FIGS. 9&10 clearly illustrate the advantage and the effectiveness of the novel bio-reactor. The modifications made in the constructional features of the present bio-reactor are not obvious to a person skilled in the art and the present constructional features should not be considered as mere replacement of different parts.

Difference Between the Present Invention with the Earlier Patents

The present invention differs from the earlier Patents of U.S. Pat. Nos. 5,030,573, dt. Jul. 9, 1991; 5,846,829, dt. Dec. 8, 1998; 5,885,826, dt. Mar. 23, 1999; 4,760,028, dt. Jul. 26, 1988; 4,840,905, dt. Jun. 20, 1989; 5,075,234, dt. Dec. 24, 1991; 6,001,642, dt. Dec. 14, 1999; 5,403,742, dt. Apr. 4, 1995; 5,885,826, dt. Mar. 23, 1999; 5,846,829, dt. Dec. 8, 1998 and 6,008,010, dt. Dec. 28, 1999 with respect to the followings:

1) the present invention involves plant organ culture which is a differentiated tissue whereas the others involve only plant cell culture;
2) the present invention involves culture of specific plant organ ("Hairy root") which is transgenic and carries a foreign DNA whereas the others involve normal plant cells in the form of callus/suspension;
3) The present invention involves transgenic hairy root cultures which are fast growing, auxin autotrophic and genetically and biochemically stable in comparison to the callus/suspension cells which have otherwise been involved by the earlier patents;
4) the present invention involves transgenic hairy root cultures which need minimum nutritional requirements with no hormonal supplementation for up-scaling in bio-reactors which otherwise reduces the cost of the practice, while on the other hand, the use of callus/suspension culture (as has been used in earlier patents) incurs higher cost due to the use of full strength media and hormonal support;
5) the present invention involves use of specific type of impeller(s) at specific position in order to ensure sufficient nutrient/oxygen supply to roots over larger dimensions whereas the earlier patents do not involve use of any such system since they do not face the problem of gas/liquid phase channeling;
6) the present invention involves the use of a support matrix in order to ensure even distribution of the roots and for their anchorage whereas the earlier patents involve either a filter near the bottom of the reactor (U.S. Pat. No. 5,030,578) or have used electromagnetic field to hold bioparticles which comprise plant cells in alginate gel along with magnetically susceptible particles (stainless steel particles) [U.S. Pat. Nos. 5,846,829 and 5,885,826];
7) Lastly, the present invention involves the production of the desired secondary metabolites within the tissue itself necessitating the process for its harvesting whereas the earlier patents mention release of such compound in to the medium by permeabilization of the plasma membrane and the tonoplast without killing the cell.

Advantages

The bioreactor configuration provides the future prospects of hairy root up-scaling in bioreactor.

1. The design modifications will help in overcoming the problem of damage caused to growing roots by shearing effect of the impeller.
2. The radial and axial flow of the marine impeller will help in the efficient distribution of oxygen and nutrients to the regions of highest tissue densities within the bio-reactor.
3. The provision of double sparger helps in the distribution of oxygen throughout the culture vessel even through the compact matrix of hairy roots.

We claim:

1. A bio-reactor for growing a plant biomass using a closed sterile vessel having a medium, said reactor comprising a vessel including a central shaft, a support matrix oriented horizontally and dividing the vessel into an upper chamber and a lower chamber, a stiffer comprising turbine-2, 4, 6 impeller, marine blade impeller or helical blade impeller mounted onto the central shaft and located at a predetermined distance from the support matrix so as to generate both radially and axially directed volumetric flow of the medium, and at least two semi-circular spargers located both in the upper compartment and lower compartment of the vessel at a predetermined distance from the support matrix.

2. A bio-reactor for growing genetically transformed hairy root plants in a culture medium without use of growth regulators, which comprises a glass culture vessel for aqueous growth medium having a central shaft, and inner side wall which is radially symmetrical about a central vertical axis, at least one elongated baffle assembly fixed in an offset position on of the vessel, so as to subdivide the inner side wall into equal parts and to cause rotary transport of radially flowing aqueous medium contained in the vessel and to prevent vortex formation; said culture vessel being divided into a lower compartment and an upper compartment by fixing a support matrix on the at least one baffle assembly to prevent damage, disformation, shearing and subsequent loss of productive capacity of hairy roots; two marine blade impellers being positioned on the central shafts one of said two marine blade impellers in the upper chamber within a predetermined distance from a head plate and dipped in the medium, and other of said two marine blade impellers in the lower chamber at a predetermined distance above the end of the central shaft, to cause both axial and radial flow of aqueous medium contained in the vessel, and two elongated semi-circular spargers, one of said two elongated semi-circular spargers is located in upper chamber and the other of said two elongated semi-circular semi-circular spargers is located in the lower chamber of the vessel for the purpose of proper oxygenation of the culture medium.

3. A bio-reactor as claimed in claim 1 wherein the plants are medicinal plants.

4. A bio-reactor as claimed in claim 2 wherein the baffle assembly comprises four vertical plates connected by by at least one connector.

5. A bio-reactor as claimed in claim 2 wherein the first marine blade impeller is located on the central shaft within a distance ranging between 8–10 cm. from the head plate.

6. A bio-reactor as claimed in claim 2 wherein the second marine blade impeller is located in the lower compartment at about 4 cm above an end of the central shaft.

7. A bio-reactor as claimed in claim 1 wherein said at least two semi-circular spargers extend both in the upper and lower chambers, positioned at a predetermined distance from the central support matrix.

8. A bio-reactor as claimed in claim 2 wherein said marine impeller ensures the radial flow of air within the culture vessel for the proper mixing of air in the aqueous medium and axial flow of air bubbles to penetrate through the genetically transformed hairy root.

9. A bio-reactor as claimed in claim 3 wherein the medicinal plants are comprise *Hyoscyamus muticus, H. albus, V. wallichii, Rauwolfia. serpentina, Atropa belladonna* or *A. accuminata*.

10. A bio-reactor as claimed in claim 2 wherein the hairy root comprises transgenic roots.

11. A bio-reactor as claimed in claim 2 wherein the genetically transformed hairy root comprises Ri-T DNA.

12. A bio-reactor as claimed 2 wherein the genetically transformed hairy root of the plant is grown without the help of growth regulating hormones.

* * * * *

UNITED STATES PATENT AND TRADEMARK OFFICE
CERTIFICATE OF CORRECTION

PATENT NO. : 6,589,780 B2
DATED : July 8, 2003
INVENTOR(S) : S. Banerjee et al.

It is certified that error appears in the above-identified patent and that said Letters Patent is hereby corrected as shown below:

Column 8,
Line 25, "stiffer" should be -- stirrer --.
Line 40, delete "of".
Line 48, "shafts" should be -- shaft, --.
Line 57, delete "semi-circular" (second occurrence).
Line 63, delete "by" (second occurrence).

Column 10,
Line 2, delete "are".
Line 9, after "claimed" insert -- in claim --.

Signed and Sealed this

Second Day of March, 2004

JON W. DUDAS
*Acting Director of the United States Patent and Trademark Office*